United States Patent
Tan et al.

(10) Patent No.: US 8,652,851 B2
(45) Date of Patent: Feb. 18, 2014

(54) MULTI-ACCEPTOR MOLECULAR PROBES AND APPLICATIONS THEREOF

(75) Inventors: Weihong Tan, Gainesville, FL (US); Chaoyong Yang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 871 days.

(21) Appl. No.: 11/570,491

(22) PCT Filed: Jun. 17, 2005

(86) PCT No.: PCT/US2005/021929
§ 371 (c)(1),
(2), (4) Date: Sep. 16, 2008

(87) PCT Pub. No.: WO2006/002167
PCT Pub. Date: Jan. 5, 2006

(65) Prior Publication Data
US 2010/0248385 A1    Sep. 30, 2010

Related U.S. Application Data

(60) Provisional application No. 60/580,410, filed on Jun. 17, 2004.

(51) Int. Cl.
*G01N 21/76* (2006.01)
(52) U.S. Cl.
USPC ............ 436/172; 436/94; 436/501; 435/6.11; 435/91.1; 536/24.3; 536/25.32

(58) Field of Classification Search
None
See application file for complete search history.

(56) References Cited

U.S. PATENT DOCUMENTS

| | | | |
|---|---|---|---|
| 5,866,336 | A | 2/1999 | Nazarenko et al. |
| 6,287,765 | B1 | 9/2001 | Cubicciotti |
| 6,573,045 | B1 | 6/2003 | Karn et al. |
| 7,070,933 | B2 | 7/2006 | Browne |
| 2002/0034757 | A1 | 3/2002 | Cubicciotti |
| 2005/0196781 | A1 | 9/2005 | Robin et al. |

FOREIGN PATENT DOCUMENTS

WO    WO 2005/051967    *   6/2005

OTHER PUBLICATIONS

Shchepinov, M.S., et al, Oligonucleotide dendrimers: systhesis and use as polylabelled DNA probes, 1997, Nucleic Acids Research, vol. 25(22), pp. 4447-4454.*

* cited by examiner

*Primary Examiner* — Robert Xu
(74) *Attorney, Agent, or Firm* — Saliwanchik, Lloyd & Eisenschenk

(57) ABSTRACT

An oligonucleotide-based molecular probe includes at least one pin loop, the pin loop including a loop sequence complementary to a target sequence. A first stem sequence is attached to one end of the pin loop, the first stem having at least one fluorescent label attached thereto. A second stem sequence is attached to the other end of the pin loop. The second stem has a plurality of quencher molecules attached thereto.

8 Claims, 13 Drawing Sheets

SEQUENCE LISTING

```
<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: Synthetic

<400> SEQUENCE: 1
cctttcgctc taaatcacta tggtcgcgcg atagg                              35

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
agatttagtg ataccagcg                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
agatttagcg ataccagcg                                                19

<210> SEQ ID NO 4
<211> LENGTH: 31
<212> TYPE: DNA
<213> ORGANISM: Artificial Sequence
<220> FEATURE:
<223> OTHER INFORMATION: Synthetic

<400> SEQUENCE: 4
cctagctcta aatcactatg gtcgcgctag g                                  31

<210> SEQ ID NO 5
<211> LENGTH: 31
<212> TYPE: DNA
<213> ORGANISM: Artificial Sequence
```

-continued

```
<220> FEATURE:
<223> OTHER INFORMATION: Synthetic

<400> SEQUENCE: 5
cgcacctctg gtctgaaggt ttattggtgc g                              31

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
cgccatgaca ctagcatcgt atcagcatgg cg                             32

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
gcgagttttt tttttttttt ctcgc                                     25

<210> SEQ ID NO 8
<211> LENGTH: 34
<212> TYPE: DNA
<213> ORGANISM: Artificial Sequence
<220> FEATURE:
<223> OTHER INFORMATION: Synthetic

<400> SEQUENCE: 8
aggctacggc acgtagagca tcaccatgat cctg                           34

<210> SEQ ID NO 9
<211> LENGTH: 31
<212> TYPE: DNA
<213> ORGANISM: Artificial Sequence
<220> FEATURE:
<223> OTHER INFORMATION: Synthetic

<400> SEQUENCE: 9
gctagctcta aatcactatg gtcgcgctag c                              31
```

MULTI-ACCEPTOR MOLECULAR PROBES AND APPLICATIONS THEREOF

STATEMENT REGARDING FEDERALLY SPONSORED RESEARCH OR DEVELOPMENT

The United States Government may have certain rights in this invention pursuant to the National Institute of General Medical Sciences Contract No. R01 GM66137.

CROSS-REFERENCE TO RELATED APPLICATIONS

The present application claims the priority of U.S. Provisional Application No. 60/580,410, filed Jun. 17, 2004; and International Application No. PCT/US2005/021929, filed Jun. 17, 2005, both of which are incorporated herein by reference in their entirety.

BACKGROUND OF THE INVENTION

A useful assaying technique using stem-loop oligonucleotide probes referred to as "molecular beacons" was first disclosed as providing a rapid, quantitative assay technique by Tyagi and Kramer (Tyagi, S., F. R. Nature Biotechnology, 14, 303-308 (1996)). Molecular beacons are designed to have loop sequences which are complementary to a target nucleic acid (e.g., rRNA). The loop sequence is disposed between a first and a second stem sequence, the respective stem sequences being complements of one another. The molecular beacon includes a fluorescent molecule on the end of the first stem and a quenching molecule on the end of the second stem.

In the absence of the complementary target sequence the fluorescence upon irradiation remains low (quenched) due to physical proximity between the fluorophore and the quencher. When the complementary target sequence is present, the loop opens and the fluorophore and the quencher are no longer in physical proximity, so that the molecular probe generates a relatively strong fluorescent signal upon irradiation when the target nucleic acid sequence is present.

Because of their inherent signal transduction mechanism, molecular beacons (MBs) have many advantages over traditional DNA probes, including enhanced specificity and sensitively and the ability to detect target without separation of hybridized and non-hybridized probes. This detect-without-separation make MBs useful in situations where it is not possible or desirable to isolate the probe-target hybrids from an excess of the unhybridized probes, such as in the real time monitoring of polymerase chain reactions in sealed tubes, or in the monitoring of mRNAs in living cells.

Since the first report of the MB in 1996 by Tyagi and Kramer, great efforts have been made to improve the MB designs. The targets of the MBs have also been extended from original DNA or RNA molecules to now include a variety of protein molecules. Molecular beacons have become one of the important tools in the field of molecular biology studies, clinical diagnostics as well as biotechnologies.

The applications and potential of molecular probes relying on fluorescence resonance energy transfer (FRET) to detect and report binding to target molecules in general have been hindered by low sensitivity. Theoretically, molecular beacons should have up to 200 times of enhancement in fluorescence signal over traditional DNA probes. However, this enhancement has rarely been achieved in molecular beacon applications. Low signal enhancement is believed to the result of many factors, including formation of secondary structures, sticky end pairing, presence of impurities and the low quenching efficiency of the quencher molecule in the molecular probe. Among them, the former two factors could be eliminated by careful design of the probe sequences. The latter two factors are major sources of the background signal.

SUMMARY OF THE INVENTION

Molecular probes that specifically detect DNA, RNA and/or proteins are described.

An oligonucleotide-based molecular probe includes at least one pin loop, the pin loop including a loop sequence complementary to a target sequence. A first stem sequence is attached to one end of the pin loop, the first stem having at least one fluorescent label attached thereto. A second stem sequence is attached to the other end of the pin loop. The second stem has a plurality of quencher molecules attached thereto.

In a preferred embodiment, molecular probes include antibodies and protein binding probes for protein-protein interaction and detection. Preferably, protein binding probes are systematically selected nucleic acids that have high affinity and selectivity for their target proteins. Also preferred are antibodies selected to have high affinity and selectivity for their protein targets. Fluorescence steady state and polarization measurements are used for signal transduction. In steady state, the protein binding probe is labeled with two fluorophores that have overlapping excitation and emission spectra. When bound to the target protein, the binding-induced conformational change of the protein binding probe causes two fluorophores to be in close proximity and change their fluorescence intensity because of fluorescence resonance energy transfer (FRET). This process can be used to report the presence of the target protein without labeling it. By determining the fluorescence of either one of the two fluorophores, a fluorescence quenching assay or a fluorescence generating assay can be used, depending on the specific application. In the polarization measurements, the protein binding probe is labeled with only one fluorophore. Binding to a much larger protein target results in a slower diffusional rotation of the protein binding probe and increased fluorescence anisotropy of the fluorophore.

Without wishing to be bound by theory, this result may be explained that the fluorophore is quenched by the nucleic acid bases of the protein binding probe. Binding to the protein can alleviate the fluorophore from the quenching environments and cause a restored fluorescence.

In another preferred embodiment, a method for detecting the presence of a target proteins in a sample comprises protein binding probes or antibodies (referred to herein as protein binding probes) bound to a support, each protein binding probe having a first end attached to the support, and a binding region that binds to a specific enantiomer of the target molecule, wherein the binding regions of different protein binding probes bind to different enantiomers of the target molecule. However, target molecules can also be determined in a solution. Protein binding probes can also be designed with a binding region that binds to a specific binding site of the target, wherein the binding regions of different protein binding probes bind to different binding sites. For example, the target can be an antigen, and the different binding sites can be different epitopes of the antigen, or the target can be a bacteria, and the different binding sites can be different surface proteins of the bacteria.

The invention further features a system for simultaneously detecting the presence of a plurality of different non-nucleic acid target molecules in a sample. The system includes a solid support (optional); a plurality of different protein binding probes, optionally bound to the support, each protein binding probe having a first end attached to the support, a binding region that binds to a specific non-nucleic acid target molecule, the binding regions of different protein binding probes binding to different target molecules; and a detection system that detects the presence of target molecules bound to protein binding probes, the detection system including a radiation source, e.g., a laser, and a detector. The system can further include an analyzer for determining the presence of target molecules in the sample based on the output of the detection system. The analyzer can also include a computer processor programmed to compare the output of the detection system to a library of known outputs corresponding to exposing samples of known composition to the protein binding probes on the solid support; and select a combination of known outputs that most closely matches the assay outputs. The computer processor can be further programmed to compare any deviation between the output of the detection system and the combination of known outputs to a library of known deviations, the known deviations being caused by known abnormal conditions; and deduce the presence or absence of known abnormal conditions.

In yet another aspect, the invention features a method or system for simultaneously detecting the presence or absence of one or more different target molecules in a sample using a plurality of different species of protein binding probes, wherein each species of protein binding probes has a different reporter group, a binding region that binds to a specific non-nucleic acid target molecule, and wherein the binding regions of different protein binding probes bind to different target molecules; and a detection system that detects the presence of target molecules bound to protein binding probes, the detection system being able to detect the different reporter groups. The method can also be carried out with a plurality of identical protein binding probes. For example, each protein binding probe can include a reporter such as a molecular beacon that changes fluorescence properties upon target binding. Each species of protein binding probe can be labeled with a different fluorescent dye to allow simultaneous detection of multiple target molecules, e.g., one species might be labeled with fluorescein and another with rhodamine. The fluorescence excitation wavelength (or spectrum) can be varied and/or the emission spectrum can be observed to simultaneously detect the presence of multiple targets.

The fluorescence measurement can be performed with a number of different instruments, including standard fluorescence spectrophotometers, or in a small volume using a high-intensity source, such a laser, high-efficiency light collection optics, such as a high-numeric aperture microscope objective, and a high-efficiency low-noise detector, such as photo-multiplier tube, a photodiode or a CCD camera.

In another aspect, the invention features a device for simultaneously detecting the presence of a plurality of different, non-nucleic acid target molecules in a sample. The devices include: a solid support; and a plurality of different protein binding probes bound to the support, each protein binding probe having a first end attached to the support, and a binding region that binds to a specific non-nucleic acid target molecule, wherein the binding regions of different protein binding probes bind to different target molecules. In these devices, the solid support can be a glass surface to which the first ends of the protein binding probes are covalently bound. In addition, the solid support can be a planar surface, and the protein binding probes can be distributed on the planar surface in a two-dimensional array. Spots of identical protein binding probes can be located at different points in the two-dimensional array.

The binding region of at least one of the protein binding probes in the device can be configured to bind to a non-nucleic acid target molecule selected from the group consisting of a protein, a small organic molecule, nucleic acid molecules, and an inorganic molecule. The protein binding probes can comprise RNA, DNA, modified RNA, modified RNA, or a combination thereof. In addition, each protein binding probe can comprise a reporter group, such as a fluorophore, for signaling binding of a target molecule to the binding region and/or a quencher.

The detection systems can be used in a variety of applications, including drug testing, high-sensitivity testing for the presence of bacteria or antigens, pollution monitoring, and testing for the presence or absence of a disease.

The following definitions are provided:

As used herein, "melting temperature" is the temperature at which 50% of DNA duplex dehybridize. For example, the melting temperature referred to in FIG. 5 is the temperature at which fluorescent intensity reach 50% of its maximum, while it is the temperature at which fluorescence intensity drop to 50% of maximum for a molecular probe mixed with target. The term "stability" in reference to duplex or triplex formation generally designates how tightly a molecule binds to its intended target sequence; more particularly, "stability" designates the free energy of formation of the duplex or triplex under physiological conditions. Melting temperature is a convenient measure of duplex and/or triplex stability.

As used herein, "a", "an," and "the" include plural references unless the context clearly dictates otherwise.

The term "biomolecule" refers to DNA, RNA (including mRNA, rRNA, tRNA and tmRNA), nucleotides and nucleosides.

A base "position" as used herein refers to the location of a given base or nucleotide residue within a nucleic acid.

As used herein, the term "array" refers to an ordered spatial arrangement, particularly an arrangement of immobilized biomolecules.

As used herein, the term "addressable array" refers to an array wherein the individual elements have precisely defined x and y coordinates, so that a given element at a particular position in the array can be identified.

As used herein, the terms "probe" and "biomolecular probe" refer to a biomolecule used to detect a complementary biomolecule. Examples include antigens that detect antibodies, oligonucleotides that detect complimentary oligonucleotides, and ligands that detect receptors. Such probes are preferably immobilized on a microelectrode comprising a substrate.

As used herein, the terms "bioarray," "biochip" and "biochip array" refer to an ordered spatial arrangement of immobilized biomolecules on a microelectrode arrayed on a solid supporting substrate. Preferred probe molecules include aptamers, nucleic acids, oligonucleotides, peptides, ligands, antibodies and antigens; peptides and proteins are the most preferred probe species. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors).

As used herein, the term "aptamer" or "selected nucleic acid binding species" shall include non-modified or chemically modified RNA or DNA. The method of selection may be by, but is not limited to, affinity chromatography and the method of amplification by reverse transcription (RT) or polymerase chain reaction (PCR).

As used herein, the term "signaling aptamer" shall include aptamers with reporter molecules, preferably a fluorescent dye, appended to a nucleotide in such a way that upon conformational changes resulting from the aptamer's interaction with a ligand, the reporter molecules yields a differential signal, preferably a change in fluorescence intensity.

As used herein, the terms "ligand," "target," and "bait" are used interchangeably throughout the specification and includes any molecule that binds to the aptamer.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature* Biotechnology 19:17-18 (2001); Manoharan M., *Biochemica et Biophysica Acta* 1489:117-139 (1999); Freier S. M., *Nucleic Acid Research,* 25:4429-4443 (1997), Uhlman, E., *Drug Discovery & Development,* 3: 203-213 (2000), Herdewin P., *Antisense & Nucleic Acid Drug Dev.,* 10:297-310 (2000)); 2'-O, 3'-C-linked [3.2.0]bicycloarabinonucleosides (see e.g. N. K Christiensen, et al, *J. Am. Chem. Soc.,* 120: 5458-5463 (1998). Such analogs include synthetic nucleosides designed to enhance binding properties, e.g., duplex or triplex stability, specificity, or the like.

As used herein, the term "downstream" when used in reference to a direction along a nucleotide sequence means in the direction from the 5' to the 3' end. Similarly, the term "upstream" means in the direction from the 3' to the 5' end.

As used herein, the term "gene" means the gene and all currently known variants thereof and any further variants which may be elucidated.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The term "variant," when used in the context of a polynucleotide sequence, may encompass a polynucleotide sequence related to a wild type gene. This definition may also include, for example, "allelic", "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

As used herein, the term "mRNA" means the presently known mRNA transcript(s) of a targeted gene, and any further transcripts which may be elucidated.

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION OF THE INVENTION

Figure 1:
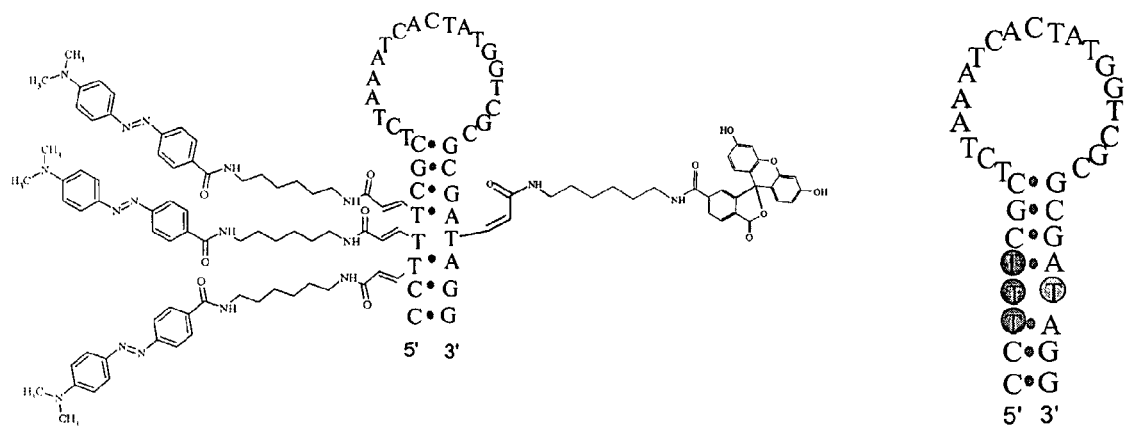
FIG. 1 shows the structure of an internally labeled three-quencher molecular beacon according to an embodiment of the invention. The nucleic acid sequence (shown twice) of the molecular beacon is SEQ ID NO: 1.

According to the invention, molecular beacons having multiple quenchers, referred to herein as either "high sensitivity molecular beacons" (HSMB) or "multi-acceptor molecular probes," and methods for forming the same are described herein. Such Multi-acceptor molecular probes provide about a 100× increase in sensitivity over traditional DNA probes, and more than a 10× increase in sensitivity over conventional single quencher molecular beacon probes. Such sensitivity enables Multi-acceptor molecular probes to be used in a variety of applications to provide improved results, including gene expression study, intracellular protein monitoring, and early cancer diagnosis, particularly where high sensitivity detection methods are required. The signal enhancement provided by Multi-acceptor molecular probes provides higher accuracy, reduces time and cost for molecular beacon sequence selection, design and preparation, as well as improves the overall productivity of the research where molecular beacons are used.

For a conventional molecular beacon probe, only a single quencher is provided. The quencher is attached to one of the two stem sequences which are attached to the loop. In contrast, Multi-acceptor molecular probes according to the invention include a plurality of attached quenchers, such as two or three, or more quenchers. The multiple quenchers can be attached to a single base, or a plurality of bases can each have a single quencher, or some bases can have a single quencher while other bases can have multiple quenchers.

Although not needed to practice the claimed invention, Applicants, not seeking to be bound to theory, present the following explanation for the improved performance of Multi-acceptor molecular probes according to the invention as compared to conventional MBs. Integrating multiple quenchers in a single molecular beacon sequence is believed to have at least two important effects. First, increasing the number of quencher molecules adjacent to a fluorophore has been found to greatly increase the overall quenching ability of the MB at closed state. Second, multiple quenchers in the molecular beacon helps improve the purity of molecular beacons. The hydrophobicity of the quencher molecules will greatly increase the retention time of the molecular beacon in the reverse phase HPLC, which will significantly improve the separation efficiency. Overall, the introduction of multiple quenchers in a molecular beacon according to the invention has been found to effectively reduce background fluorescence by significantly increasing quenching efficiency of MB and improving the purity of MB.

The loop sequence can include DNA, RNA, or related segments. The first and second stems are generally complementary DNA, RNA or PNA sequences. Typically, the middle loop sequence will include 16 to 25 bases, while the stems will generally each include from 5 to 8 bases. However, loop sequences and stem sequence lengths can be above or below these ranges.

A variety of fluorescent dyes and quenchers can be used with the invention. Suitable quenchers include DABCYL(4-(4-(dimethylamino)phenylazo) benzoic acid), QSY™ (such as QSY-9 and QSY-35 (Invitrogen, Carlsbad, Calif.)), ECLIPSE™ (Epoch Biosciences, Bothell, Wash.) and BLACK HOLE QUENCHERS™ (BHQ; such as BHQ-1, 2, and 3 (Biosearch Technologies, Inc. Novato Calif.)) can be useful quenchers. Both QSY™ and BHQ™ provide specific quencher species for different emission ranges. Other quenchers are possible. A variety of fluorescent dyes may also be used with the invention. Suitable fluorescent dyes include Fluorescein ($C_{20}H_{12}O_5$, Spiro(isobenzofuran-1(3H), 9'-(9H)-xanthen)-3-one, 3',6'-dihydroxy-), Oregon Green ($C_{20}H_{10}F_2O_5$, Spiro[isobenzofuran-1(3H), 9'-[9H]xanthen]-3-one, 2',7'-difluoro-3',6'-dihydroxy-), Cy3 (Amersham Biosciences Corp, Piscataway, N.J.), and TMR ($C_{24}H_{23}N_2O_3$.Cl, Tetramethylrhodamine). Other fluorescent dyes are possible.

Multiple quenchers can be attached to the end of molecular beacons with a dendrimer linker. Different numbers of quenchers can be attached, for example. The number of quenchers can be controlled by using different numbers and different types of dendrimer phosphoramidite. Trebler phosphoramidite, $C_{86}H_{101}N_2O_{14}P$, Tris-2,2,2-[3-(4,4'-dimethoxytrityloxy) propyloxymethyl]ethyl-[(2-cyanoethyl)-(N,N-diisopropyl)]-phosphoramidite, and doubler phosphoramidite, $C_{64}H_{79}N_4O_{10}P$, 1,3-bis-[5-(4,4'-dimethoxytrityloxy)pentylamido]propyl-2-[(2-cyanoethyl)-(N,N-diisopropyl)]-phosphoramidite, are among the dendrimer phosphoramidites that can be used to form multiple-quencher moieties. These phosphoramidites are commercially available. The coupling of dendrimer linker on a DNA synthesizer is known in the art. The linker can be coupled to a DNA sequence with the same procedure as a regular base except for a longer coupling time, usually about 15 minutes.

Fluorophore and quencher pairs should preferably be selected so as to possess spectrum overlap, so that the emission spectrum of the fluorophore overlaps with the absorption spectrum of the quencher. multi-acceptor molecular probe's assembled from DABCYL quenchers have excellent quenching efficiency for fluorophores with emission around 450-550 nm, such as Fluorescein (FAM), Oregon Green, and Cy3. multi-acceptor molecular probe's assembled from Eclipse quenchers are useful for dyes which emit around 480-600 nm, such as Fluorescein, Oregon Green, Cy3, and TMR.

Two exemplary methods for labeling multiple quenchers to a molecular beacon molecule are described herein. In a first method, resulting in a product referred to as design A, the quencher DABCYL dT, $C_{63}H_{76}N_9O_{10}P$, 5'-dimethoxytrityloxy-5-[(N-4'-carboxy-4-(dimethylamino)-azobenzene)-aminohexyl-3-acrylimido]-2'-deoxyUridine-3'-[(2-cyanoethyl)-(N,N-diisopropyl)]-phosphoramidite is used to form Multi-acceptor molecular probes having multiple quenchers according to the invention, such as the multi-acceptor molecular probe shown in FIG. 1. The multi-acceptor molecular probe shown in FIG. 1 includes three quenchers, all being DABCYL molecules, which are internally attached to 5' arm of molecular beacon. The fluorophore is internally labeled and is attached to the 3' end of the molecular beacon. In the structure at the right FIG. 1, the dark circles stand for DABCYL labeled dT, while the darker circle on the 3' end stands for the fluorescein labeled dT.

The synthesis of multiple quencher molecular beacons shown in design A can be achieved automatically or manually. When fluorophore and quencher labeled nucleotide monomers are used, the entire synthesis can be performed on a DNA synthesizer automatically. The fluorophore labeled nucleotide monomers can be coupled as a normal nucleotide base with a coupling time recommended by the manufacturer. Functional group labeled nucleotide monomers, such as amine labeled dT phosphoramidite, or thiol labeled dT phosphoramidite, can be used to couple fluorophore or quencher molecules manually when the desired fluorophore or quencher labeled nucleotide monomers are not available. The post-synthesis treatments of molecular beacons, including deprotection, desalting, and purification, follow the same known procedures that are used to produce conventional molecular beacons. Summation of the extinction coefficient of the oligonucleotide sequence with that of all quenchers and fluorophores at 260 nm is preferably used to quantitate the product.

In a second method, resulting in a product referred to as design B, dendrimer phosphoramidites are used. Trebler phosphoramidite, $C_{86}H_{101}N_2O_{14}P$, Tris-2,2,2-[3-(4,4'-dimethoxytrityloxy) propyloxymethyl]ethyl-[(2-cyanoethyl)-(N,N-diisopropyl)]-phosphoramidite, and doubler phosphoramidite, $C_{64}H_{79}N_4O_{10}P$, 1,3-bis-[5-(4,4'-dimethoxytrityloxy)pentylamido]propyl-2-[(2-cyanoethyl)-(N,N-diisopropyl)]-phosphoramidite, are among the dendrimer phosphoramidites that can be used to form multiple quencher moieties. The phosphoramidite couples quencher molecules to form Multi-acceptor molecular probes having multiple quenchers according to the invention, such as to form the multi-acceptor molecular probe shown in FIG. 2. The 5' of the oligonucleotide is shown attached to three DABCYL molecules, while the 3' is labeled with a fluorescein molecule. In the structure on right, the dark balls stand for DABCYL molecules, while the dark ball on the 3' end stands for the fluorescent molecule.

To synthesize Multi-acceptor molecular probes such as that shown in design B, dendrimeric phosphoramidite can be used to couple multiple quencher molecules at the end of the molecular beacon. The synthesis can start with a fluorophore CPG column. Bases are then coupled one by one as programmed in a DNA synthesizer. Following the coupling of the last base, dendrimeric phosphoramidite is coupled before quencher molecules are coupled. The dendrimeric phosphoramidite generates multiple reactive OH groups for coupling of quencher molecules. Using this method, there is no need to use a special CPG column. Dendrimeric phosphoramidite and quencher phosphoramidite are coupled in a regular way as normal bases except extended coupling time is used (e.g. 15 minutes) to ensure high coupling efficiency.

If the fluorophore CPG or quencher phosphoramidites are not available, phosphoramidites with cross-linking functional groups such as thiol phosphoramide, and amine phosphoramidite can be used for the further attaching of fluorophore or quenchers manually. The post-synthesis treatments of molecular beacon, including deprotection, desalting, and purification, follow the same known procedures that are used to produce conventional molecular beacons. Summation of the extinction coefficient of the oligonucleotide sequence with that of all quenchers and fluorophores at 260 nm is preferably used to quantitate the product.

Figure 3:
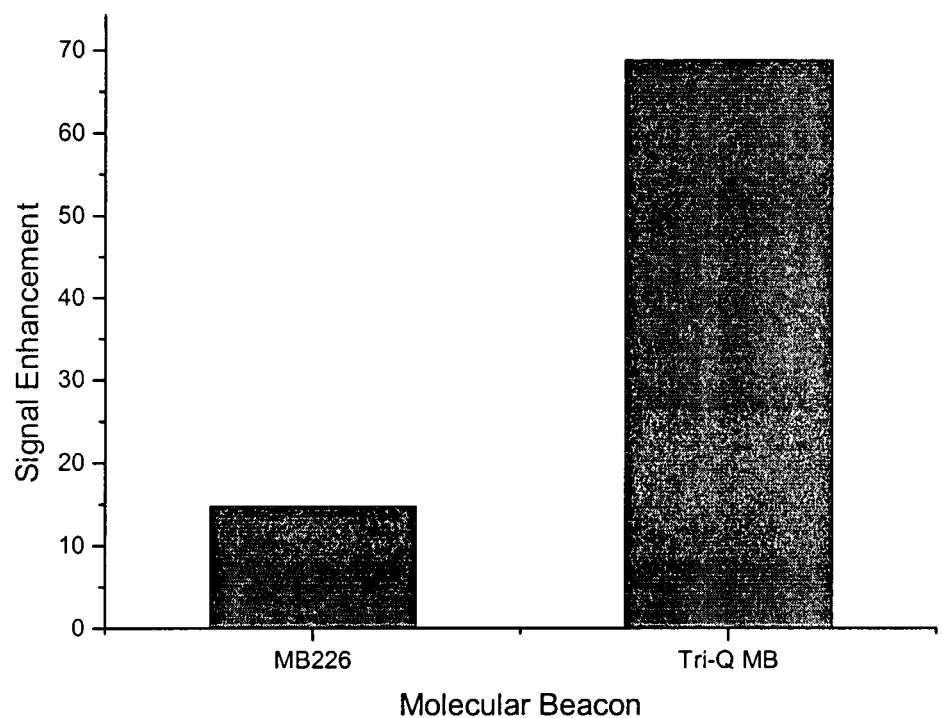
FIG. 3 shows the signal-to-noise ratio for the molecular beacon with 3 quenchers shown in FIG. 1 (Tri-Q MB) as compared to MB226, a conventional single-quencher molecular beacon.
Figure 4:
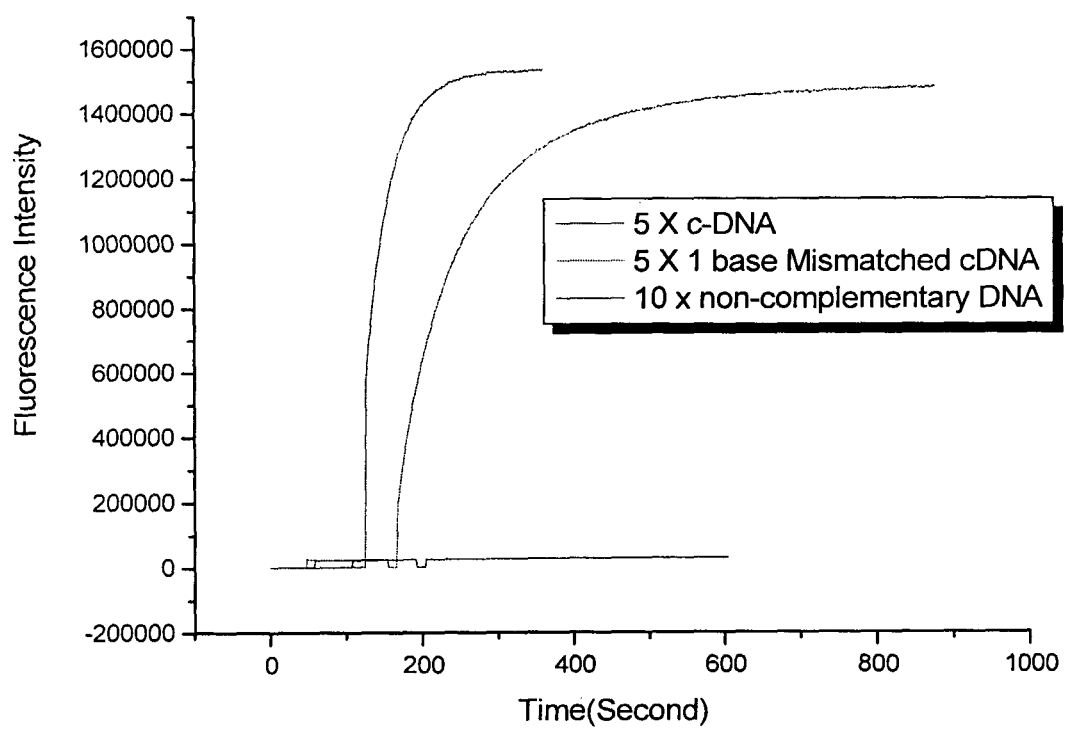
FIG. 4 shows the response of 65 nM of the molecular beacon with 3 quenchers shown in FIG. 1 to 325 nM perfect matched DNA (complementary to its loop), single base mismatched DNA and 10 times concentration of random sequence DNA.

Results obtained for Multi-acceptor molecular probes according to the invention comprising a three quencher molecular beacon based on the multi-acceptor molecular probe shown in FIG. 1 demonstrated a 70 fold signal enhancement upon hybridization to its target DNA, which is 5 times higher than that of a regular molecular beacon of same loop sequence and same stem stability. The multi-acceptor molecular probe synthesized with this new design demonstrated high selectivity while also demonstrating single mismatch discrimination capability (FIGS. 3 and 4, respectively). FIG. 3 shows about a five times improvement of signal-to-noise ratio for the molecular beacon with 3 quenchers shown in FIG. 1 (Tri-Q MB) as compared to MB226, a conventional molecular beacon. In both cases, the molecular beacons were at 65 nM, and the c-DNA concentration used was 325 nM. These two beacons had the same loop sequence to recognize the same target DNA, and was designed to have similar stem stability. FIG. 4 shows the response of 65 nM of the molecular beacon with 3 quenchers shown in FIG. 1 to 325 mM perfect matched DNA (complementary to its loop), single base mismatched DNA and 10 times concentration of random sequence DNA. The addition of perfect matched DNA produced about 68.7 times of signal change while the signal enhancement for the single mismatched one is about 62.6. There is no evident signal change upon the addition 10× random sequence DNA.

Figure 5:
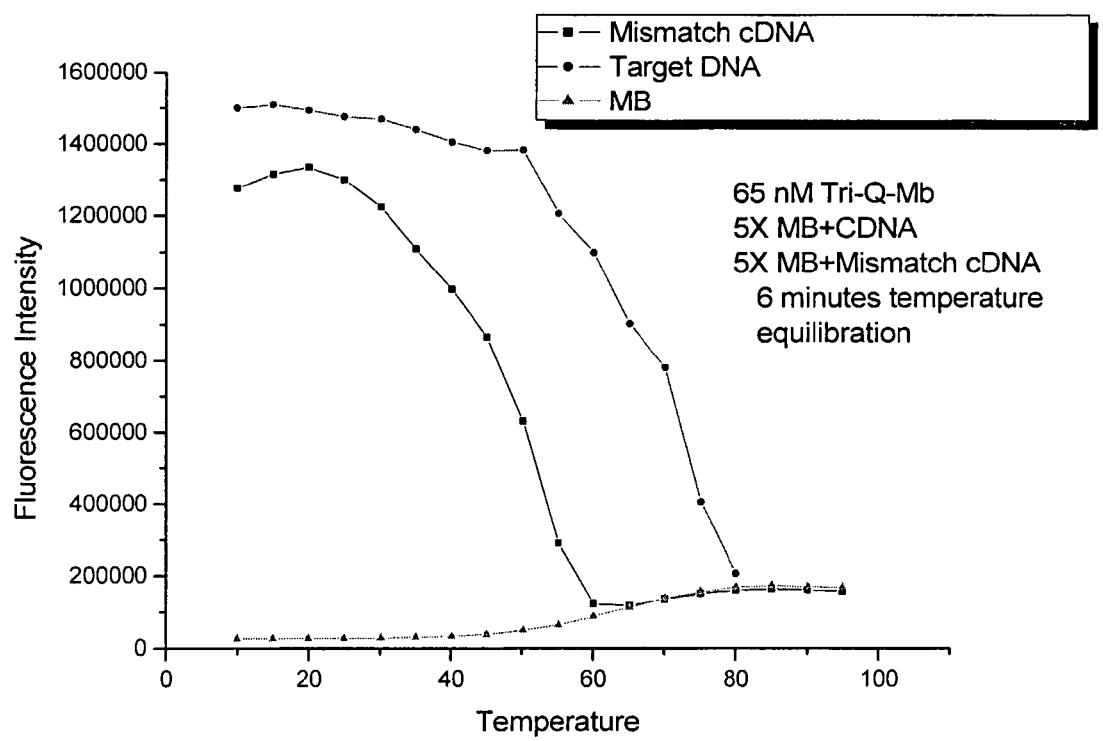
FIG. 5 is a fluorescent intensity vs. temperature in degrees C. curve showing melting temperature obtained from the molecular beacon with 3 quenchers shown in FIG. 1.

FIG. 5 is a fluorescent response vs. temperature curve showing melting temperature curve in degrees C. obtained from the molecular beacon with 3 quenchers shown in FIG. 1. The top plot is a solution of 65 nM of this molecular beacon with 325 nM of target DNA. The middle one is 65 nM of this molecular beacon and 325 nM of c-DNA with one single mismatched. The lowest line is the solution of this molecular beacon by itself. The sequence of this molecular beacon is 5'-CCT(D)T(D)T(D)CGC TCT AAA TCA CTA TGG TCG C GCGAT(FAM)AGG, (SEQ ID NO: 1) the underlines standing for the stem sequence. The sequences of target sequence and mismatch cDNA are AGA TTT AGT GAT ACC AGC G (SEO ID NO: 2) and AGA TTT AGC GAT ACC AGC G, (SEQ ID NO: 3) respectively.

Figure 2:
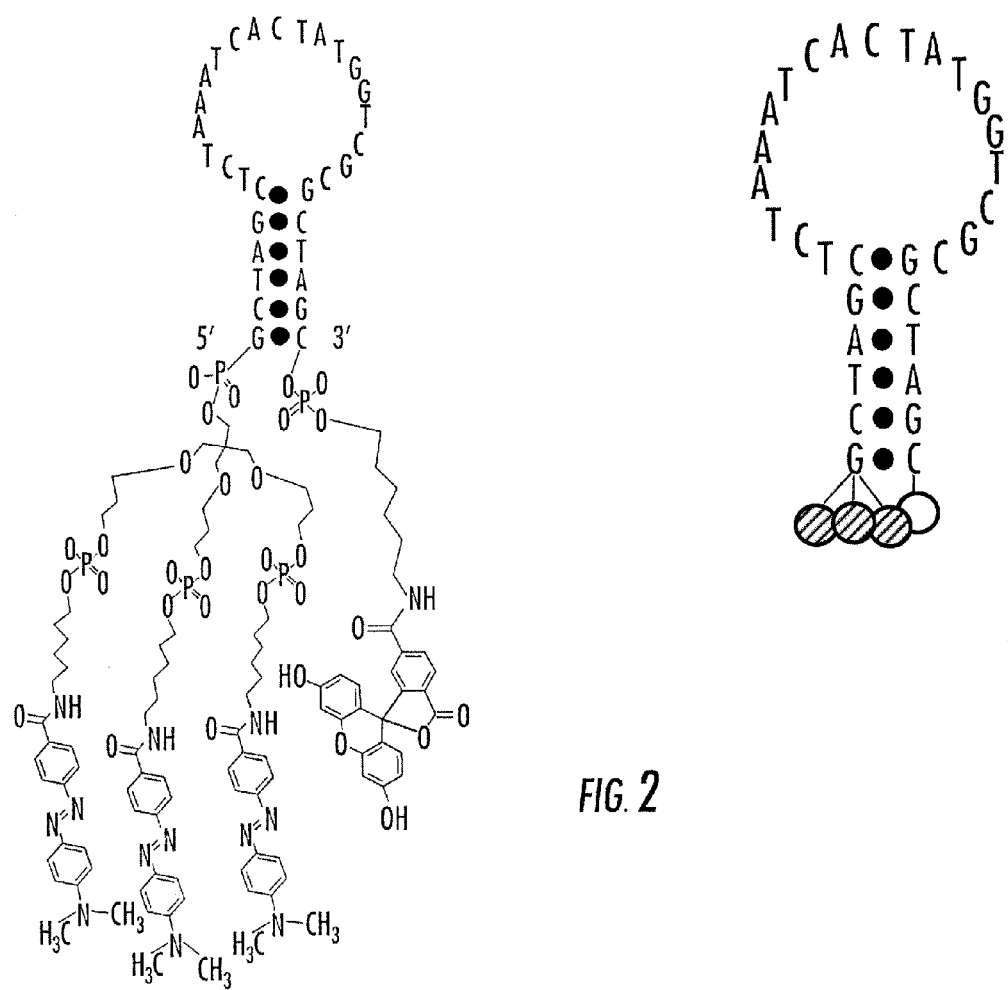
FIG. 2 shows the structure of a dendrimer quencher labeled molecular beacon according to another embodiment of the invention. The nucleic acid sequence (shown twice) of the molecular beacon is SEQ ID NO: 9.
Figure 6:
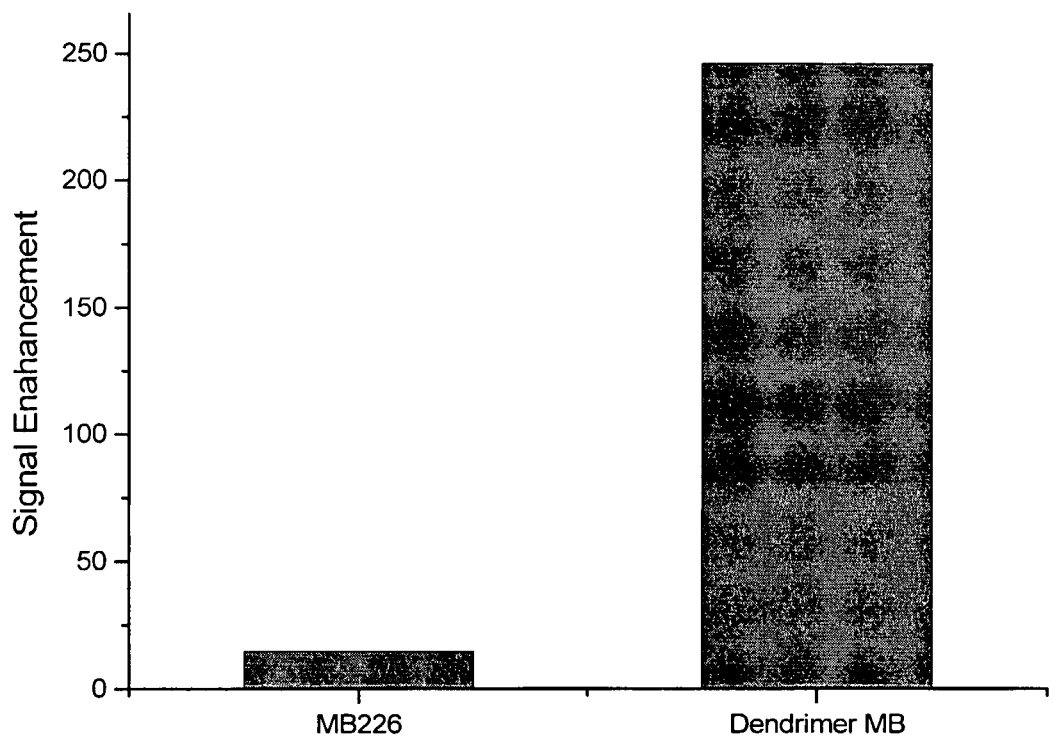
FIG. 6 shows signal enhancement for the beacon with 3 quenchers shown in FIG. 2 as compared to a convention molecular beacon MB226.

The molecular beacon as shown in FIG. 2 was found to provide a signal enhancement as high as 250 times upon hybridization with its c-DNA. FIG. 6 shows signal enhancement for the multi-acceptor molecular probe with 3 quenchers shown in FIG. 2 as compared to a conventional molecular beacon MB226. In both cases, the molecular beacons were at 65 nM, and the c-DNA concentration used was 325 nM. These two beacons had the same loop sequence to recognize the same target DNA, and shared the same stem sequences. The signal enhancement of the molecular beacon according to the invention was found to be 250 times of enhancement upon hybridization, compared to 15 times of that from regular beacon, MB226.

Figure 7:
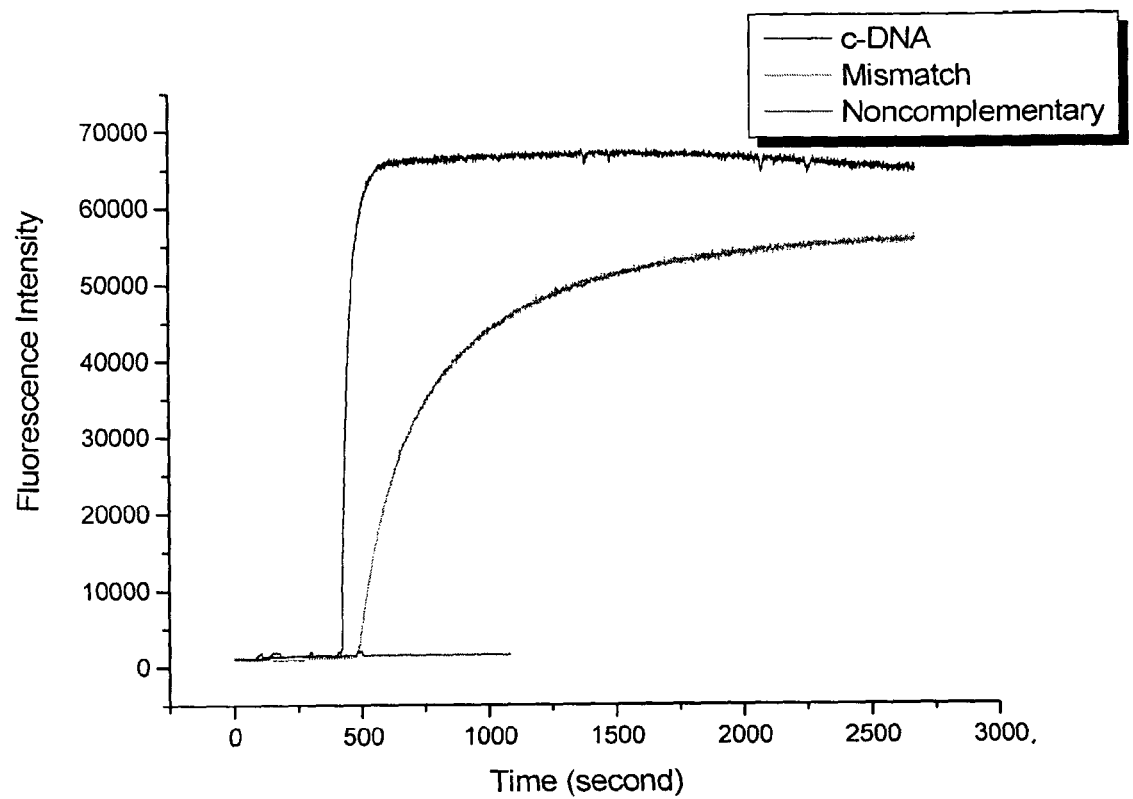
FIG. 7 shows the response of 65 nM for the beacon with 3 quenchers shown in FIG. 2 to 325 µM perfect matched DNA (complementary to its loop), single base mismatched DNA and 10 times concentration of random sequence DNA.

FIG. 7 shows the response of 65 nM for the beacon with 3 quenchers shown in FIG. 2 to 325 nM perfect matched DNA (complementary to its loop), single base mismatched DNA and 10 times concentration of random sequence DNA. The addition of perfect matched DNA produced about 250 times of signal change while the signal enhancement for the single mismatched one was about 200. There was no evident signal change upon the addition of 10× random sequence DNA. FIG. 7 also shows that the multi-acceptor molecular probe shown in FIG. 2 provides high selectivity and also has single mismatch discrimination capability.

The multi-acceptor molecular probes of the invention can provide enhanced stability. The stem portion of a multi-acceptor molecular probe holds the quencher and fluorophore together at room temperature. When the temperature of the solution is raised, the stem will dehybridize, and the hairpin structure of the probe will become a random coil. Multi-acceptor molecular probes according to the invention stabilize the stem so that it only dehybridizes at higher temperatures. The stability of the hairpin structure can be characterized by the melting temperature. It was found that the melting temperature of an multi-acceptor molecular probe that consists of three quenchers was about 5° C. higher that that of a molecular beacon with a single quencher. This stabilization is a result of hydrophobic interaction between the multiple quenchers and the fluorophore. The more quenchers the multi-acceptor molecular probe has, the stronger the interaction will likely be.

Figure 8:
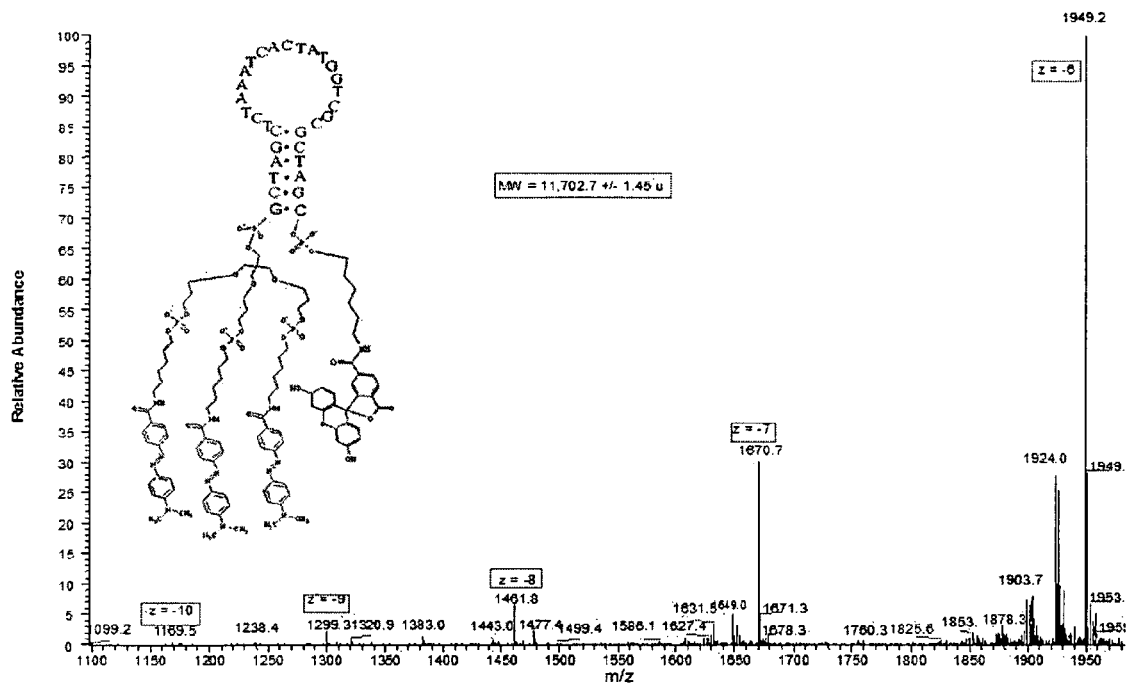
FIG. 8 is the negative ESI mass spectrum of a multi-quencher/FAM labeled multi-acceptor molecular probe shown in FIG. 1. The nucleic acid sequence of the molecular probe is SEQ ID NO: 9.

The Multi-acceptor molecular probes synthesized were analyzed with reverse phase gradient C8 HPLC/UV/ESI-MS. The oligonucleotides yielded $[M-zH]^{z-}$ ions in (−)ESI-MS. The molecular masses were calculated from the multiple charge ion spectra, all of which matched the molecular weight calculated from the product structures. FIG. 8 is the negative ESI mass spectrum of a multiquencher/FAM labeled multi-acceptor molecular probe. The observed molecular weight of this multi-acceptor molecular probe was 11,702.7 g/mol, which matched well with calculated molecular weight (11701.5 g/mol).

Figure 9A:
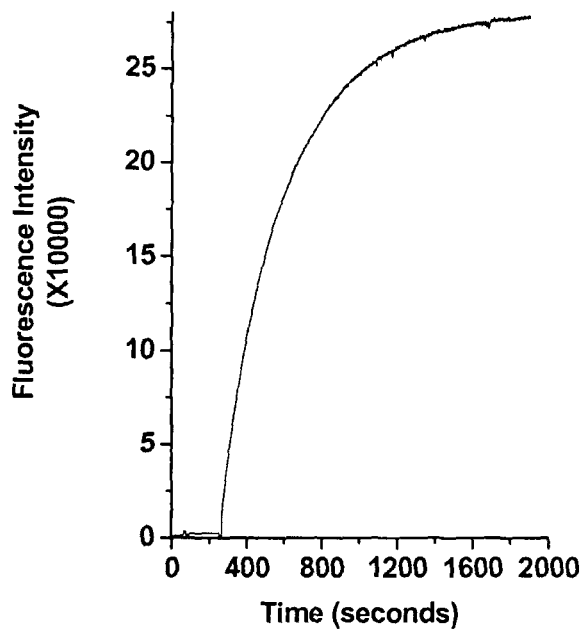
FIG. 9 shows the response of 65 nM of Cy3 labeled triple-quencher multi-acceptor molecular probe to 325 nM of target DNA (A) and a comparison of signal-to-background (S/B) ratio of triple quencher Cy3 multi-acceptor molecular probe to that of single quencher Cy3 (B).
Figure 9B:
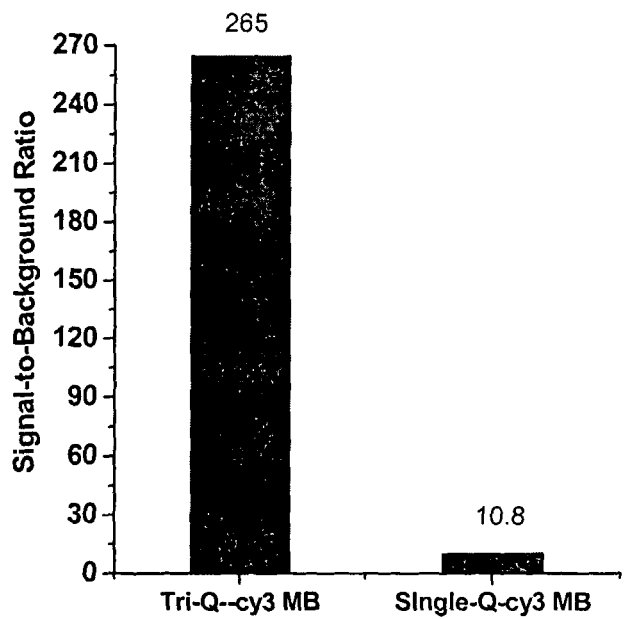

The multi-acceptor molecular probe can be used with different fluorophores with excellent quenching efficiency. Multi-acceptor molecular probes were prepared with fluorophores such as TMR and Cy3. Excellent S/Bs were observed for all these dyes. FIG. 9 shows (A) the response of 65 nM of Cy3 labeled triple-quencher multi-acceptor molecular probe to 325 nM of target DNA and (B) a comparison of SIB of triple quencher Cy3 multi-acceptor molecular probe to that of single quencher Cy3 (B). As shown in FIG. 9, the multi-acceptor molecular probe with Cy3 showed more than 250-fold of signal change upon target hybridization. Both multi-acceptor molecular probes had the same sequence except different quenchers were used (Quencher-CC TAG CTC TAA ATC ACT ATG GTC GCG CTA GG-Cy3 (SEQ ID NO: 4)). All hybridization experiments were carried out in 20 mM Tris-HCl buffer (pH7.5, 50 mM NaCl and 5 mM $MgCl_2$).

Figure 10:
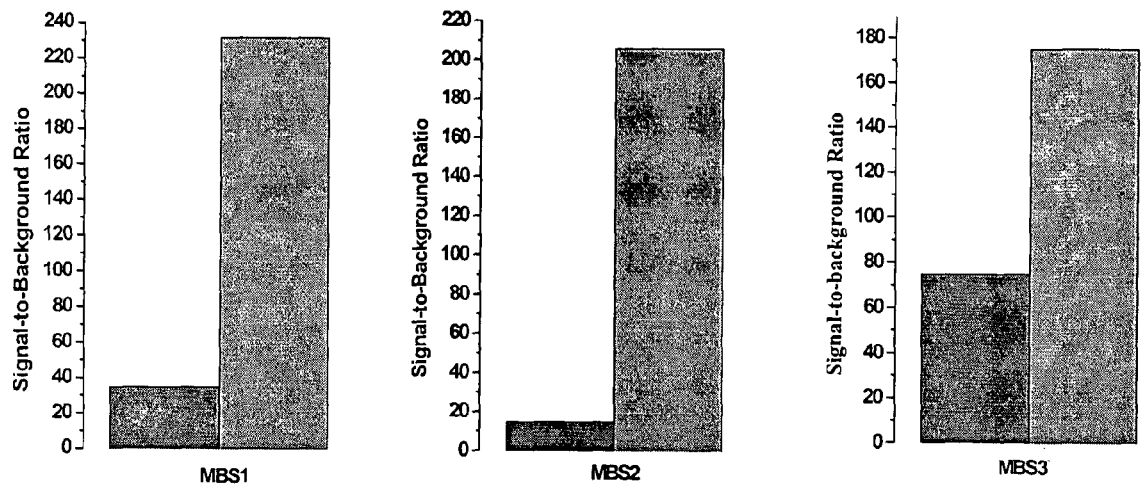
FIG. 10 shows a comparison of signal-to-background (S/B) ratio of molecular beacons labeled with three quenchers (light shading) to those of MB labeled with normal quenchers (MBS1, MBS2) or gold nanoparticle (MBS3).

Three molecular beacons reported in the literature were synthesized. The sequences of these molecular beacons were listed in Table 1. Multiquenchers were used in the synthesis instead of the reported quenchers. FIG. 10 shows a comparison of S/B ratio of molecular beacons labeled with three quenchers to those (light shading) of MB labeled with normal quenchers (MBS1, MBS2) or gold nanoparticle (MBS3).

TABLE 1

Molecular Beacon Sequences

| MB | Source | Sequence |
|---|---|---|
| MBS1 | Methods Mol Biol 212, 111 | FAM-CGCACCTCTGGTCTGA AGGTTTATTGGTGCG-DAB CYL (SEQ ID NO: 5) |
| MBS2 | Antisense Nucleic Acid Drug Dev 12, 225 | FAM-CGCCATGACACTAGCA TCGTATCAGCATGGCG-DABCYL (SEQ ID NO: 6) |
| MBS3 | Nat Biotechnol 19, 365 | FAM-GCGAGTTTTTTTTTTT TTTCTCGC-Gold (SEQ ID NO: 7) |

FIG. 10 shows a comparison of S/B ratio of molecular beacons labeled with three quenchers to those (light shading) of MB labeled with normal quenchers (MBS1, MBS2) or gold nanoparticle (MBS3).

Figure 11A:
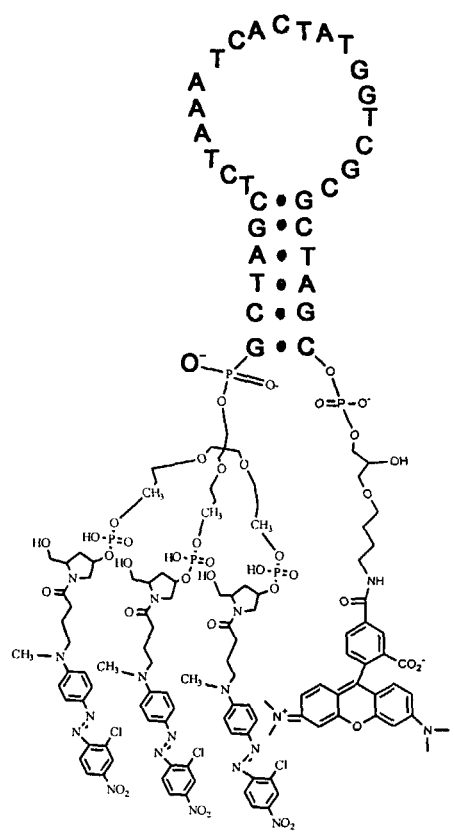
FIG. 11 shows (A) the structure of a molecular beacon with three Eclipse quenchers and (B) the fluorescent response after hybridization of this molecular beacon with target DNA. The nucleic acid sequence of the molecular beacon is SEQ ID NO: 9.
Figure 11B:
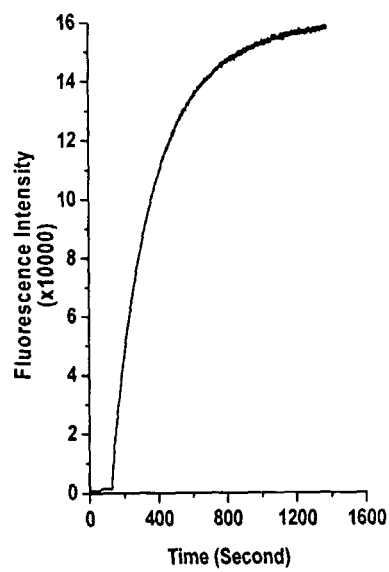

The approach of providing a chemically assembled macromolecule from individual quenchers to yield a better quencher moiety can be extended to other quencher molecules. For example, a multiquencher consisting of three Eclipse quenchers quenched 99.6% of fluorescence from TMR in a multi-acceptor molecular probe. FIG. 11 shows (A) the structure of a molecular beacon with three Eclipse quenchers and (B) fluorescent intensity after hybridization of this molecular beacon with target DNA.

The molecular assembling approach of the invention can be extended to assemble macromolecules for better molecular signaling and recognition. One example would be a super-ligand assembled from low affinity ligands. The linking of two or more weak binding ligands can result in a multi-dentate or super-ligand with greatly improved binding affinity. Examples of such ligands include antibodies and protein binding probes. The formation constant of such a super-ligand is expected to be the product of the formation constant of each individual ligand. The concept can be demonstrated comparing the formation constant of Mg-EDTA and Mg—NTA. EDTA, $(HOOCH_2C)_2NCH_2CH_2N(CH_2COOH)_2$, is a four dentate ligand. The formation constant of Mg-EDTA is $4.90 \times 10^8$. A tri-dentate ligand, nitrilotriacetic acid NTA $N(CH_2COOH)_3$ has a formation constant of about $2.6 \times 10^5$ to form a complex with magnesium ions. A ligand with higher binding affinity is desired for many applications, such as molecular signaling, disease treatment, and biological studies.

Protein Interactions

The molecular probes of the invention are also used to detect protein interactions. As used herein, the terms "probe" and "biomolecular probe" refer to a biomolecule used to detect a complementary biomolecule, e.g. multi-acceptor molecular probe. Examples include antigens that detect antibodies, oligonucleotides that detect complimentary oligonucleotides, and ligands that detect receptors. Such probes are preferably immobilized on a microelectrode comprising a substrate.

Figure 12:
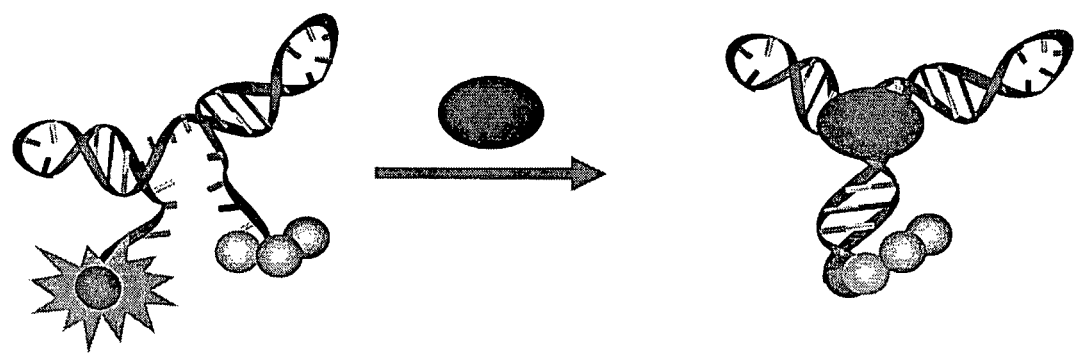
FIG. 12 is a schematic representation of binding of a molecular probe (aptamer) to a target protein.

The multi-quencher approach can be extended to other FRET based molecular probes. Dendrimeric quenchers comprising three DABCYLs were used to label one termini of a synthetic DNA aptamer ((DABCYL)$_3$-AGGCTACG-GCACGTAGAGCATCACCATGATCCTG-FAM (SEQ ID NO: 8)) for the B-chain of platelet derived growth factor (PDGF). Aptamers are short single-stranded oligonucleotide sequences selected to bind to essentially any molecular targets with high selectivity and affinity through an in vitro selection process called SELEX (Selective Evolution of Ligands by EXponential enrichment). Besides their excellent binding affinity and selectivity, other characteristics endow aptamers with great potential for use in protein analysis. An aptamer was selected to bind selectively to PDGF with high affinity. The difference from a molecular beacon, is that this aptamer changes its conformation from open form to close form upon binding to PDGF protein, which bringing the quencher moiety close to the fluorophore moiety (See, for Example, FIG. 12).

Figure 13:
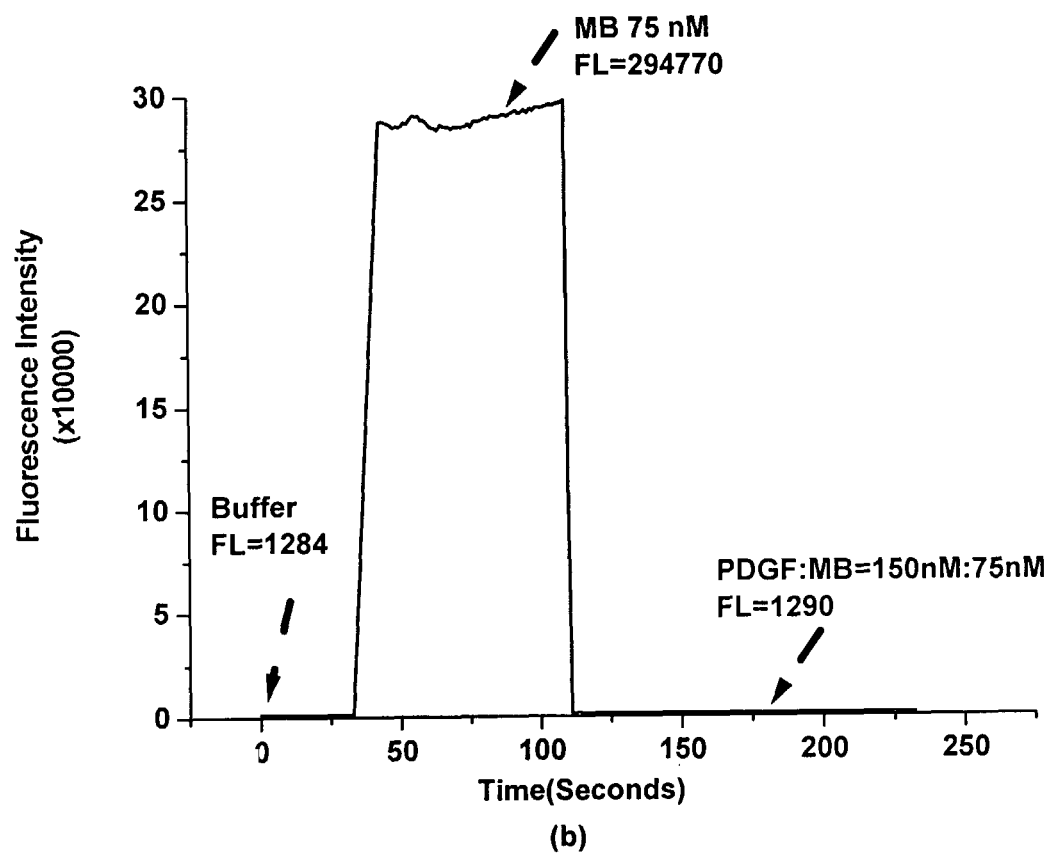
FIG. 13 is a graph showing the response of a dendrimeric aptamer probe to the addition of a specific target protein (PDGF-BB).

As a result of the conformation change, the fluorescence intensity from the fluorophore decreases. FIG. 13 shows the response of the dual labeled aptamer, 5' with three DABCYL molecules while 3' with Fluorescein, to the addition of PDGF-BB. Upon binding to PDGF, the dendrimeric quencher labeled aptamer underwent change of fluorescent intensity from 294770 to buffer background, where fluorescent intensity changed by a factor of more than 49,000 times. It also indicated the quenching efficiency of the dendrimeric quencher to Fluoresein is greater than 99.99%. This is a dramatically improvement considering that binding of a same aptamer with single DABCYL label to PDGF only introduces less than 20 fold signal changes.

Aptamer polynucleotides are typically single-stranded standard phosphodiester DNA (ssDNA). Close DNA analogs can also be incorporated into the aptamer as described below.

A typical aptamer discovery procedure is described below:
1) A polynucleotide comprising a randomized sequence between "arms" having constant sequence is synthesized. The arms can include restriction sites for convenient cloning and can also function as priming sites for PCR primers. The synthesis can easily be performed on commercial instruments. 2) The target protein is treated with the randomized polynucleotide. The target protein can be in solution and then the complexes immobilized and separated from unbound nucleic acids by use of an antibody affinity column. Alternatively, the target protein might be immobilized before treatment with the randomized polynucleotide. 3) The target protein-polynucleotide complexes are separated from the uncomplexed material and then the bound polynucleotides are separated from the target protein. The bound nucleic acid can then be characterized, but is more commonly amplified, e.g. by PCR and the binding, separation and amplification steps are repeated. In many instances, use of conditions increasingly promoting separation of the nucleic acid from the target protein, e.g. higher salt concentration, in the binding buffer used in step 2) in subsequent iterations, results in identification of polynucleotides having increasingly high affinity for the target protein. 4) The nucleic acids showing high affinity for the target proteins are isolated and characterized. This is typically accomplished by cloning the nucleic acids using restriction sites incorporated into the arms, and then sequencing the cloned nucleic acid.

The affinity of aptamers for their target proteins is typically in the nanomolar range, but can be as low as the picomolar range. That is KD is typically 1 pM to 500 nM, more typically from 1 pM to 100 nM. Apatmers having an affinity of KD in the range of 1 pM to 10 nM are also useful.

Aptamer polynucleotides can be synthesized on a commercially available nucleic acid synthesizer by methods known in the art. The product can be purified by size selection or chromatographic methods.

Aptamer polynucleotides are typically from about 10 to 200 nucleotides long, more typically from about 10 to 100 nucleotides long, still more typically from about 10 to 50 nucleotides long and yet more typically from about 10 to 25 nucleotides long. A preferred range of length is from about 10 to 50 nucleotides.

The aptamer sequences can be chosen as a desired sequence, or random or partially random populations of sequences can be made and then selected for specific binding to a desired target protein by assay in vitro. Any of the typical nucleic acid-protein binding assays known in the art can be used, e.g. "Southwestern" blotting using either labeled oligonucleotide or labeled protein as the probe. See also U.S. Pat. No. 5,445,935 for a fluorescence polarization assay of protein-nucleic acid interaction.

Appropriate nucleotides for aptamer synthesis and their use, and reagents for covalent linkage of proteins to nucleic acids and their use, are considered known in the art.

A desired aptamer-protein complex can be labeled and used as a diagnostic agent in vitro in much the same manner as any specific protein-binding agent, e.g. a monoclonal antibody. Thus, an aptamer-protein complex of the invention can be used to detect and quantitate the amount of its target protein in a sample, e.g. a blood sample, to provide diagnosis of a disease state correlated with the amount of the protein in the sample.

A desired aptamer-target molecular complex can also be used for diagnostic imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{88}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$P can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Aptamer Selection

Aptamers configured to bind to specific target molecules can be selected, e.g., by synthesizing an initial heterogeneous population of oligonucleotides, and then selecting oligonucleotides within the population that bind tightly to a particular target molecule. Once an aptamer that binds to a particular target molecule has been identified, it can be replicated using a variety of techniques known in biological and other arts, e.g., by cloning and polymerase chain reaction (PCR) amplification followed by transcription.

The synthesis of a heterogeneous population of oligonucleotides and the selection of aptamers within that population can be accomplished using a procedure known as the Systematic Evolution of Ligands by Exponential Enrichment or SELEX. The SELEX method is described in, e.g., Gold et al., U.S. Pat. Nos. 5,270,163 and 5,567,588; Fitzwater et al., "A SELEX Primer," Methods in Enzymology, 267:275-301 (1996); and in Ellington and Szostak, "In Vitro Selection of RNA Molecules that Bind Specific Ligands," Nature, 346: 818-22. Briefly, a heterogeneous DNA oligomer population is synthesized to provide candidate oligomers for the in vitro selection of aptamers. This initial DNA oligomer population is a set of random sequences 15 to 100 nucleotides in length flanked by fixed 5' and 3' sequences 10 to 50 nucleotides in length. The fixed regions provide sites for PCR primer hybridization and, in one implementation, for initiation of transcription by an RNA polymerase to produce a population of RNA oligomers. The fixed regions also contain restriction sites for cloning selected aptamers. Many examples of fixed regions can be used in aptamer evolution. See, e.g., Conrad et al., "In Vitro Selection of Nucleic Acid Aptamers That Bind Proteins," Methods in Enzymology, 267:336-83 (1996); Ciesiolka et al., "Affinity Selection-Amplification from Randomized Ribooligonucleotide Pools," Methods in Enzymology, 267:315-35 (1996); Fitzwater, supra.

Aptamers are selected in a 5 to 100 cycle procedure. In each cycle, oligomers are bound to the target molecule, purified by isolating the target to which they are bound, released from the target, and then replicated by 20 to 30 generations of PCR amplification.

Aptamer selection is similar to evolutionary selection of a function in biology. Subjecting the heterogeneous oligonucleotide population to the aptamer selection procedure described above is analogous to subjecting a continuously reproducing biological population to 10 to 20 severe selection events for the function, with each selection separated by 20 to 30 generations of replication.

Modified Aptamers

Heterogeneity is introduced, e.g., at the beginning of the aptamer selection procedure, and does not occur throughout the replication process. Alternatively, heterogeneity can be introduced at later stages of the aptamer selection procedure.

Various oligomers can be used for aptamer selection, including, e.g., 2'-fluoro-ribonucleotide oligomers, $NH_2$-substituted and $OCH_3$-substituted ribose aptamers, and deoxyribose aptamers. RNA and DNA populations are equally capable of providing aptamers configured to bind to any type of target molecule. Within either population, the selected aptamers occur at a frequency of 109 to 1013, see Gold et al., "Diversity of Oligonucleotide Functions," Annual Review of Biochemistry, 64:763-97 (1995).

Using 2'-fluoro-ribonucleotide oligomers is likely to increase binding affinities ten to one hundred fold over those obtained with unsubstituted ribo- or deoxyribo-oligonucleotides. See Pagratis et al., "Potent 2'-amino and 2' fluoro 2'deoxyribonucleotide RNA inhibitors of keratinocyte growth factor" Nature Biotechnology, 15:68-73. Such modified bases provide additional binding interactions and increase the stability of aptamer secondary structures. These modifications also make the aptamers resistant to nucleases, a significant advantage for real world applications of the system. See Lin et al., "Modified RNA sequence pools for in vitro selection" Nucleic Acids Research, 22:5229-34 (1994); Pagratis, supra.

Modified aptamers are aptamers having at least two types of nucleotides, such as both deoxyribonucleotides and ribonucleotides, ribonucleotides and modified nucleotides, or two different types of modified nucleotides. One form of an aptamer is peptide nucleic acid/nucleic acid aptamer (PNA/ NAP). For example, 5'-PNA-DNA-3' or 5'-PNA-RNA-3' aptamers may be used. The DNA and RNA portions of such aptamers can have random or degenerate sequences. Other forms of aptamers are, for example, 5'-(2'-O-Methyl)RNA-RNA-3' or 5'-(2'-O-Methyl)RNA-DNA-3'.

Many modified nucleotides (nucleotide analogs) are known and can be used in aptamer synthesis. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to locked nucleic acids (LNA), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O- S- or N-alkynyl; or O-alkyl-O-alkyl, wherein the alkyl, alkenyl and alkynyl may be substituted or unsubstituted C1 to C10, alkyl or C2 to $C_{10}$ alkenyl and alkynyl. 2' sugar modifications also include but are not limited to —O[$(CH_2)_n$O]$_m$CH$_3$, —O$(CH_2)_n$OCH$_3$, —O$(CH_2)_n$NH$_2$, —O$(CH_2)_n$CH$_3$, —O$(CH_2)$, —ONH$_2$, and —O$(CH_2)_n$ON[$(CH_2)_n$CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S, Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can comprise inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only comprise a single modification, but may also comprise multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science 254:1497-1500 (1991)).

Aptamers can comprise nucleotides and can be made up of different types of nucleotides or the same type of nucleotides. For example, one or more of the nucleotides can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can comprise bases (that is, the base portion of the nucleotide) and can (and normally will) comprise different types of bases.

In another preferred embodiment, the invention provides for aptamer labeling techniques. Methods for the molecular aptamers's application have been developed for detecting biomarkers, small molecules and drugs and for protein interactions. Aptamers have been developed as molecular probes for easy and effective detection of small drug molecules, proteins and inter-molecular interactions. Compared with previous techniques, the methods disclosed herein, have enabled aptamers to have high sensitivity and extremely high selectivity for their targets. Aptamers are highly stable and can be easily modified for different signal transduction mechanisms.

Aptamers are nucleic acid oligonucleotides that may be selected using a systematic evolution of ligands via an exponential enrichment (SELEX) process (Tuerk, C. & Gold L. (1990) Science 249, 505-510; Ellington, A. D. & Szostak, J. W. (1990) Nature 346, 818-822). Compared to antibodies, aptamers can have similar affinity to their protein targets but are much smaller and much easier to produce. Quite tolerant to external environment changes and internal modifications, aptamers can be conveniently labeled for various applications.

In another preferred embodiment, the invention provides unique biolabeling methods and bioanalytical techniques that can use aptamers efficiently for disease-related protein, small molecules and biomarkers and for high throughput protein-protein interaction studies.

In another preferred embodiment, aptamers as disease markers are developed for drug related small molecules and for bioanalysis. Aptamers of the invention are useful in areas such as disease diagnosis and therapeutics, small molecule detection, drug discovery and in biomedical and biotechnological studies.

In another preferred embodiment, the invention provides aptamers for protein-protein interaction and detection. Preferably, aptamers are systematically selected nucleic acids that have high affinity and selectivity for their target proteins. The methods described herein, enable label-free analysis of proteins in real time and homogeneous solutions based on aptamers. Fluorescence steady state and polarization measurements are used for signal transduction. For example, in steady state, the aptamer is labeled with two fluorophores that have overlapping excitation and emission spectra. When bound to the target protein, the binding-induced conformational change of the aptamer causes two fluorophores to be in close proximity and change their fluorescence intensity because of fluorescence resonance energy transfer (FRET). This process can be used to report the presence of the target protein without labeling it. By looking at the fluorescence of either one of the two fluorophores, a fluorescence quenching assay or a fluorescence generating assay depending on the specific application is used. In the polarization measurements, the aptamer is labeled with only one fluorophore. Binding to a much larger protein target results in a slower diffusional rotation of the aptamer and increased fluorescence anisotropy of the fluorophore. The methods have demonstrated highly sensitive protein detection with excellent selectivity in real time using both FRET and anisotropy approaches.

In another preferred embodiment, aptamers determine protein functions. For example, in a competitive assay, the aptamer/target protein binding complex can be disrupted by a third molecule, either a protein or a drug molecule, if the third molecule can interact with the target protein. This protein-molecule interaction can be readily reflected in real time by changes in the fluorescent signals of the aptamer. By analyzing FRET or anisotropy of the dye-labeled aptamer, protein-protein and protein-small molecule interactions in homogeneous solution can be monitored.

In another preferred embodiment, the invention provides for aptamer based assays in determining protein and drug molecule interactions. Fluorescence assays for protein analysis and protein function study are easily adapted to large-scale formats, such as a 96-well array, for high-throughput protein study. Diagnoses of diseases including cancers can be carried out by identify certain protein markers that are present in the cells. By developing aptamers for different cancer marker proteins, bioarrays that have the capability of sensitive multiplex cancer marker detection can be developed. Based on the aptamer assay, the analysis of the cell content is highly efficient. The fluorescence signals obtained from the array generate a pattern which shows the presence of different cancer related proteins. By comparing the patterns acquired from different cell samples, cancer diagnoses can be accomplished with great ease and accuracy.

In another preferred embodiment, the invention provides for the dequenching of fluorophores bound to aptamers used in real time protein detection. Protein-binding aptamer based assays have been shown, herein, to be capable of sensitive protein detection in real time. Preferably, the signal transduction mechanisms used in such detection include fluorescence resonance energy transfer (FRET) and fluorescence anisotropy (FA). For example, in FRET, a fluorophore and a quencher are labeled on the aptamer and a protein-binding induced conformational change of the aptamer is required to trigger a fluorescence signal change. In FA, two polarizers are needed which causes much lower detected fluorescence intensity compared to steady state measurements. A small dynamic range is usually another problem with FA for sensitive protein detection. Some fluorophores, when attached to certain positions on the aptamer, could display a significant fluorescence enhancement upon protein binding. Without wishing to be bound by theory, this result may be due to the quenching of the fluorophore by the nucleic acid bases of the aptamer. Binding to the protein can alleviate the fluorophore from the quenching environments and cause a restored fluorescence.

Fluorescence resonance energy transfer (FRET) occurs between the electronic excited states of two fluorophores when they are in sufficient proximity to each other, in which the excited-state energy of the donor fluorophore is transferred to the acceptor fluorophore. The result is a decrease in the lifetime and a quenching of fluorescence of the donor species and a concomitant increase in the fluorescence intensity of the acceptor species. In one application of this principle, a fluorescent moiety is caused to be in close proximity to a quencher molecule. Donor and acceptor molecules operate in a set wherein one or more acceptor molecules accepts energy from one or more donor molecules, or otherwise quenches signal from the donor molecule, when the donor and acceptor molecules are closely associated. In one embodiment, the donor and acceptor molecules are about 30 to about 200 Å apart or about 10 to about 40 nucleotides apart. Transfer of energy may occur through collision of the closely associated molecules of a set, or through a non-radiative process such as fluorescence resonance energy transfer (FRET). For FRET to occur, transfer of energy between donor and acceptor molecules requires that the molecules be close in space and that the emission spectrum of a donor have substantial overlap with the absorption spectrum of the acceptor (Yaron et al. Analytical Biochemistry, 95, 228-235 (1979), the teachings of which are incorporated herein by reference). Alternatively, intramolecular energy transfer may occur between very closely associated donor and acceptor molecules (e.g., within 10 Å) whether or not the emission spectrum of a donor molecule has a substantial overlap with the absorption spectrum of the acceptor molecule (Yaron et al.) This process is referred to as intramolecular collision since it is believed that quenching is caused by the direct contact of the donor and acceptor molecule (Yaron et al.).

Because the efficiency of both collision and non-radiative transfer of energy between the donor and acceptor molecules is directly dependent on the proximity of the donor and acceptor molecules, formation and dissociation of the complexes of this invention can be monitored by measuring at least one physical property of at least one member of the set which is detectably different when the complex is formed, as compared with when the aptamers and target/bait exist independently and unassociated. Preferably, the means of detection will involve measuring fluorescence of an acceptor fluorophore of a set or the fluorescence of the donor fluorophore in a set containing a fluorophore and quencher pair (e.g. a donor and acceptor). While not wishing to be bound by theory, the fluorescent molecules may interact with one another via hydrophobic interactions, thereby reducing the adverse effect of distance between the donor and acceptor fluorescent molecules. Thus, fluorescence energy transfer can occur when the donor and acceptor fluorescent molecules are up to about 40 nucleotides away from each other.

In one embodiment of the present invention, the 3'-end of the aptamer is labeled with N,N1,N,N1-tetramethyl-6-carboxy rhodamine (TAMRA). Donor and acceptor molecules suitable for FRET are well known in the art (see page 46 of R. P. Haugland, Handbook of Fluorescent Probes and Research Chemicals, 6th ed.; Molecular Probes, Oregon, the teachings of which are incorporated herein by reference). Typically, to obtain fluorescence resonance energy transfer, the donor fluorescent molecule has a shorter excitation wavelength than the acceptor fluorescent molecule and the donor emission wavelength overlaps with the acceptor excitation wavelength, to allow transfer of energy from the donor to the acceptor. Preferred fluorophores are fluorescein and derivatives thereof, such as 5-(2'-aminoethyl)-aminoapthalene-1-sulfonic acid (EDANS) and rhodamine and derivatives thereof such as Cy3, Cy5 and Texas Red. Suitable donor/acceptor pairs are, for example, fluorescein/tetramethyrhodamine, IAEDANS/fluorescein and EDANS/DABCYL. In another embodiment of the present invention, the same fluorescent molecule is used for the donor and acceptor. In this embodiment, the wavelength used to excite the detection complexes is polarized. Unpolarized emission detected is indicative of FRET. In this embodiment, it is preferable to remove unincorporated labeled nucleotides (e.g., by washing) to improve the detection signal.

Detection Labels

To aid in detection and quantitation of molecules, detection labels can be directly incorporated into aptamers or can be coupled to detection molecules. As used herein, a detection label is any molecule that can be associated with aptamers, directly or indirectly, and which results in a measurable, detectable signal, either directly or indirectly. A label may be any moiety covalently attached to an oligonucleotide or nucleic acid analog. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

A preferred class of labels are detection labels, which may provide a signal for detection of the labeled oligonucleotide by fluorescence, chemiluminescence, and electrochemical luminescence. Fluorescent dyes useful for labeling oligonucleotides include fluoresceins, rhodamines, cyanines, and metal porphyrin complexes. Preferred fluorescein dyes include 6-carboxyfluorescein (6-FAM), 2',4',1,4-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-caroxyflurescein (NED), 2'-chloro-7'-phenyl-1,4-dichloro-6-carboxyfluorescein (VIC), and (JODA). The 5-carboxyl, and other regio-isomers, may also have useful detection properties. Fluorescein and rhodamine dyes with 1,4-dichloro substituents are especially preferred.

Another preferred class of labels include quencher moieties. The emission spectra of a quencher moiety overlaps with a proximal intramolecular or intermolecular fluorescent dye such that the fluorescence of the fluorescent dye is substantially diminished, or quenched, by fluorescence resonance energy transfer (FRET). Oligonucleotides which are intramolecularly labeled with both fluorescent dye and quencher moieties are useful in nucleic acid hybridization assays, e.g. the "Taqman™" exonuclease-cleavage PCR assay.

Particularly preferred quenchers include but are not limited to (i) rhodamine dyes selected from the group consisting of tetramethyl-6-carboxyrhodamine (TAMRA), tetrapropano-6-carboxyrhodamine (ROX), and (ii) DABSYL, DABCYL, cyanine dyes including nitrothiazole blue (NTB), anthraquinone, malachite green, nitrothiazole, and nitroimidazole compounds and the like.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4-tetrachlorofluorescein (TET), 2',4',5',7',1, 4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Examples of other suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY™, Cascade Blue™, Oregon Green™, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—$CH_3$, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodarmine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodanine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Additional labels of interest include those that provide for signal only when the aptamer with which they are associated is specifically bound to a target molecule, where such labels include: "molecular beacons" as described in Tyagi & Kramer, *Nature Biotechnology* (1996) 14:303 and EP 0 070 685 B1. Other labels of interest include those described in U.S. Pat. No. 5,563,037; WO 97/17471 and WO 97/17076.

Labeled nucleotides are a preferred form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951:157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)).

Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

Those of ordinary skill in the art will recognize that labeled, unlabeled and modified nucleotides are readily available for the method of the present invention. They can be synthesized using commercially available instrumentation and reagents or they can be purchased from numerous commercial vendors of custom manufactured oligonucleotides.

Aptamers have great potential in molecular recognition due to their excellent structural stability and exceptional flexibility with various intra-molecular modifications. While previous work has been focused on using aptamers as probes for direct detection of their target molecules, this invention describes novel applications for aptamers in areas where understanding of the interactions between known proteins and other molecules bears great significance.

In another preferred embodiment, aptamers are labeled with a fluorophore and a quencher to form intra-molecular FRET. Preferably, the folded conformations of the are stabilized by binding to their target molecules and produce a fluorescence signal change of the fluorophore induced by FRET when the aptamer binds to its target. Preferably, the target-binding induced FRET cause between about 40% up to 100% fluorescence quenching.

In another preferred embodiment, FRET can be formed within an aptamer even if the aptamer lacks the necessary conformational changes accompanying the binding to the target molecules.

Solid-State Detectors

Solid-state detectors are solid-state substrates or supports to which aptamers or detection molecules have been coupled. A preferred form of solid-state detector is an array detector. An array detector is a solid-state detector to which multiple different aptamers or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin films or membranes, beads, bottles, dishes, fibers, optical fibers, woven fibers, chips, compact disks, shaped polymers, particles and microparticles. A chip is a rectangular or square small piece of material. Preferred forms for solid-state substrates are thin films, beads, or chips.

Aptamers immobilized on a solid-state substrate allow capture of the products of the disclosed amplification method on a solid-state detector. Such capture provides a convenient means of washing away reaction components that might interfere with subsequent detection steps. By attaching different aptamers to different regions of a solid-state detector, different targets can be captured at different, and therefore diagnostic, locations on the solid-state detector. For example, in a multiplex assay, aptamers specific for numerous different targets (each representing a different target sequence amplified via a different set of primers) can be immobilized in an array, each in a different location. Capture and detection will occur only at those array locations corresponding to aptamers for which the corresponding target sequences were present in a sample.

Methods for immobilization of oligonucleotides to solid-state substrates are well established. Oligonucleotides, including aptamers and detection probes, can be coupled to substrates using established coupling methods. For example, suitable attachment methods are described by Pease et al., Proc. Natl. Acad. Sci. USA 91(11):5022-5026 (1994), and Khrapko et al., Mol. Biol. (Mosk) (USSR) 25:718-730 (1991). A method for immobilization of 3'-amine oligonucleotides on casein-coated slides is described by Stimpson et al., Proc. Natl. Acad. Sci. USA 92:6379-6383 (1995). A preferred method of attaching oligonucleotides to solid-state substrates is described by Guo et al., Nucleic Acids Res. 22:5456-5465 (1994). Examples of nucleic acid chips and arrays, including methods of making and using such chips and arrays, are described in U.S. Pat. Nos. 6,287,768, 6,288,220, 6,287,776, 6,297,006, and 6,291,193 which are hereby incorporated by reference.

Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

This invention can be embodied in other forms without departing from the spirit or essential attributes thereof and, accordingly, reference should be had to the following claims rather than the foregoing specification as indicating the scope of the invention.

We claim:

1. A molecular probe, comprising: at least one pin loop, said pin loop having two ends and including a loop sequence complementary to a target sequence;
   a first stem sequence attached to the one end of said pin loop, said first stem having at least one fluorescent label attached thereto, and
   a second stem sequence attached to the other end of said pin loop, said second stem having a plurality of quencher molecules attached to a single terminal base of the second stem sequence, wherein a dendrimer phosphoramidite is used to link said single base to said plurality of quencher molecules, wherein said quencher molecules and fluorescent label(s) possess spectrum overlap.

2. The probe of claim 1, wherein said dendrimer phosphoramidite is at least one selected from the group consisting of Tris-2,2,2-[3-(4,4'-dimethoxytrityloxy) propyloxymethyl] ethyl-[(2-cyanoethyl)-(N,N-diisopropyl)]-phosphoramidite, and 1,3-bis-[5-(4,4'-dimethoxytrityloxy)pentylamido]propyl-2-[(2-cyanoethyl)-(N,N-diisopropyl)]-phosphoramidite.

3. A detection system comprising:
   at least one excitation light source providing excitation radiation; and
   at least one molecular probe, comprising: at least one pin loop, said pin loop having two ends and including a loop sequence complementary to a target sequence;
   a first stem sequence attached to the one end of said pin loop, said first stem having at least one fluorescent label attached thereto, and
   a second stem sequence attached to the other end of said pin loop, said second stem having a plurality of quencher molecules attached to a single terminal base of the second stem sequence, wherein a dendrimer phosphoramidite is used to link said single base to said plurality of quencher molecules wherein said quencher molecules and fluorescent label(s) possess spectrum overlap.

4. A method of detecting the presence of at least one target molecule in a sample, the method comprising the steps of:

providing at least one molecular probe, comprising: at least one pin loop, said pin loop having two ends and including a loop sequence complementary to a target sequence;

a first stem sequence attached to the one end of said pin loop, said first stem having at least one fluorescent label attached thereto, and a second stem sequence attached to the other end of said pin loop, said second stem having a plurality of quencher molecules attached to a single terminal base of the second stem sequence, wherein a dendrimer phosphoramidite is used to link said single base to said plurality of quencher molecules, wherein said quencher molecules and fluorescent label(s) possess spectrum overlap;

providing the sample;

contacting the at least one molecular probe with the sample and allowing binding of the molecular probe(s) to said at least one target molecule, wherein binding of the at least one target molecule to the at least one molecular probe results in either an increase or decrease of fluorescence intensity compared to a baseline fluorescence of unbound molecular probe(s); and measuring the resultant fluorescence intensity.

5. The method of claim 4, wherein binding of the at least one molecular probe to the at least one target molecule results in a decrease of fluorescence intensity as compared to a baseline fluorescence of unbound molecular probe(s).

6. The method of claim 4, wherein binding of the at least one target molecule to the at least one molecular probe results in an increase of fluorescence intensity as compared to a baseline fluorescence of unbound molecular probe(s).

7. The method of claim 4, wherein the at least one target molecule is selected from the group consisting of protein, organic molecule, and nucleic acid molecule.

8. The probe of claim 1, wherein the molecular probe is an aptamer.

* * * * *

UNITED STATES PATENT AND TRADEMARK OFFICE
CERTIFICATE OF CORRECTION

PATENT NO. : 8,652,851 B2  
APPLICATION NO. : 11/570491  
DATED : February 18, 2014  
INVENTOR(S) : Weihong Tan et al.

Page 1 of 1

It is certified that error appears in the above-identified patent and that said Letters Patent is hereby corrected as shown below:

In the Specification

Column 8,
Line 8, "325 μM" should read --325 nM--.

Column 11,
Line 34, "325 mM" should read --325 nM--.

Column 12,
Line 50, "of SIB of" should read --of S/B of--.

Column 15,
Line 29, "$^{88}$Re," should read --$^{188}$Re,--.

Column 17,
Line 28, "O(CH$_2$)," should read --O (CH$_2$)$_n$,--.

Signed and Sealed this
First Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,652,851 B2
APPLICATION NO. : 11/570491
DATED : February 18, 2014
INVENTOR(S) : Tan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1757 days.

Signed and Sealed this

Twenty-ninth Day of September, 2015

Michelle K. Lee
*Director of the United States Patent and Trademark Office*